United States Patent [19]

Hoffmann et al.

[11] 4,390,756
[45] Jun. 28, 1983

[54] METHOD AND APPARATUS FOR GENERATING ELECTROCUTANEOUS STIMULATION PATTERNS FOR THE TRANSMISSION OF ACOUSTIC INFORMATION

[75] Inventors: Christian Hoffmann; Manfred Zollner, both of Munich; Eberhard Zwicker, Icking, all of Fed. Rep. of Germany

[73] Assignee: Siemens Aktiengesellschaft, Berlin & Munich, Fed. Rep. of Germany

[21] Appl. No.: 222,957

[22] Filed: Jan. 6, 1981

[30] Foreign Application Priority Data

Jan. 30, 1980 [DE] Fed. Rep. of Germany ....... 3003315

[51] Int. Cl.³ ............................................ H04R 25/00
[52] U.S. Cl. ............................. 179/107 BC; 128/421
[58] Field of Search ................. 179/107 BC, 107 FD, 179/107 R; 3/1, 1.1; 128/419 R, 421

[56] References Cited

U.S. PATENT DOCUMENTS 2,703,344  3/1955  Anderson ..................... 179/107 BC
4,284,856  8/1981  Hochmair et al. ........ 179/107 BC X
4,289,935  9/1981  Zollner et al. ............... 179/107 FD

*Primary Examiner*—Stafford D. Schreyer
*Attorney, Agent, or Firm*—Hill, Van Santen, Steadman, Chiara & Simpson

[57] ABSTRACT

In an exemplary embodiment, the point of departure is that of a substitute signal system for deaf individuals which codes acoustical signals, in particular speech sound, into electrocutaneous stimulation patterns. Current pulse patterns serve as substitute signals which, via skin surface electrodes, e.g. on the forearm, bring about sensory patterns which can be interpreted as speech information. To this end, the sound signal is separated with band pass filters into e.g. twelve component signals characteristic for the recognition of speech, whose levels are converted into pulse durations, whereby the dependency of the sensation intensity upon the stimulation parameters is taken into account. The mean frequencies of the band pass filters are associated with a corresponding number of locations on the forearm (i.e. in the present example twelve). A simulation of lateral inhibition suppresses irrelevant spectral components and thus acts in a selectivity-increasing (or enhancing) fashion. It is thereby possible that, after only approximately fifteen hours of practice, ten monosyllabic words are correctly recognized with a reliability of approximately 95% by means of the sensor patterns which are to be transmitted in accordance with the disclosure. The disclosed method and apparatus for its realization are particularly suited for use in hearing prostheses for deaf individuals.

23 Claims, 10 Drawing Figures

METHOD AND APPARATUS FOR GENERATING ELECTROCUTANEOUS STIMULATION PATTERNS FOR THE TRANSMISSION OF ACOUSTIC INFORMATION

BACKGROUND OF THE INVENTION

The invention relates to a method for generating electrocutaneous stimulation patterns (i.e., electric stimulation patterns which are perceptible on the skin) as carriers of acoustic information and apparatus for carrying out this method. The apparatus is particularly suited for providing the deaf (i.e., those which are hearing-impaired to a high degree) with signals which bring about sensory patterns on the skin surface which can be interpreted by the wearer as acoustic; e.g. speech information (cf. e.g. U.S. Pat. No. 2,703,344).

In the case of known hearing prostheses, in which above-cited methods are employed, the acoustic signal to be transmitted is separated by means of band-pass filters into a series of k different component signals. The latter are then modulated onto a carrier signal with a frequency of $f_T$, which lies higher than that of the signals to be transmitted. The k modulation signals thus obtained control currents which are to be supplied to k electrodes which are applied at k locations of the skin surface of the wearer of the apparatus, for example, a deaf patient.

The thus generatable chronologically and locally varying sensory patterns then provide characteristic sensory patterns for individual speech sounds, sound combinations and words. After a certain practice time, the patient can correlate therefrom the learned pattern progressions with acoustic e.g. speech events. In this manner he can differentiate spoken words. The possibility is thus provided of the patient acquiring a vocabulary for this "language" consisting of electrocutaneous signals. The prothesis can then be employed as an independently operating substitute for hearing in instances of speech communication in which a reading-off from the mouth of the speech partner ("lip reading") must be dispensed with (e.g. during telephoning or radio reception). Like apparatus for the transmission of mechanical oscillations (vibrations), it can also be employed for the purpose of reinforcing (or supporting) observation as well as for the purpose of facilitating during speech learning. However, the known apparatus have nevertheless not found widespread use in practice, which is probably based on a series of shortcomings with regard to the psychophysical conditions during electric stimulation of the skin and the correlation of the resulting sensations with speech signals.

SUMMARY OF THE INVENTION

In the case of a method according to the preamble of patent claim 1 and apparatus for carrying out said method, the object underlying the invention resides in providing an improvement in taking into account the pyschophysical conditions during the conversion of the acoustic signals into electric signals transmittable to the skin. In accordance with the invention, this object is achieved by the measures disclosed in the characterizing clause of this claim. The objects of the subclaims are expedient embodiments of the invention.

The invention proceeds from extensive investigations of the psychophysics of the transmission of acoustic information by means of electric current stimulations via the skin. This led to numerous improvements in speech signal analysis, in the further processing of the data (selection for the purpose of reduction of the intelligence to be conveyed), and in the recoding into the electric current stimulation patterns.

To this end, by means of a microphone, signals converted from acoustic signals to electric signals are supplied, following a preamplification, to a linear pre-distortion stage. The amplitudes of high frequency spectral components are raised therein relative to low frequency spectral components in order to provide a compensation for the fact that the mean spectrum of speech sound drops toward higher frequencies. The increase is to amount to at least 10 dB in order that the component levels of the two first formants in the case of bright vowels/e, i, y/ become approximately equal. Subsequently the signal is supplied to a sound volume limiter which, for sound pressure levels $L_P$ greater than approximately 60 dB, maintains the peak value of the output signal at a constant value so that the following filters are not overloaded. Simultaneously it generates a signal which represents a measure of the amplification resulting and which serves the purpose of reconstruction of the original sound level $L_P$ in the following stages.

In order to generate an electric substitute character (or signal code element) system as speech intelligence, it has proven satisfactory, in accordance with the invention, to separate the amplitude-limited sound signal into twelve component signals by means of a series of twelve band pass filters. The amplitudes of these component signals are measured in uniform chronological intervals $T_a$ of 8 to 20 ms, in particular, 10 ms. For further processing, the signals are then subjected to the actual recoding of the amplitudes of the component signals into electric stimulation current patterns. For this purpose, they are expediently supplied to a process control computer. The computer here serves as an instrument for conversion of the levels of the component signals into electric signals which are transmittable to the electrodes and in which the expected sensitivity intensities are taken into account and also irrelevant components are suppressed.

Further details and advantages shall be explained in the following on the basis of the exemplary embodiments illustrated in the Figures of the accompanying sheets of drawings; and other objects, features and advantages will be apparent from this detailed disclosure and from the appended claims.

DETAILED DESCRIPTION

Figure 1:
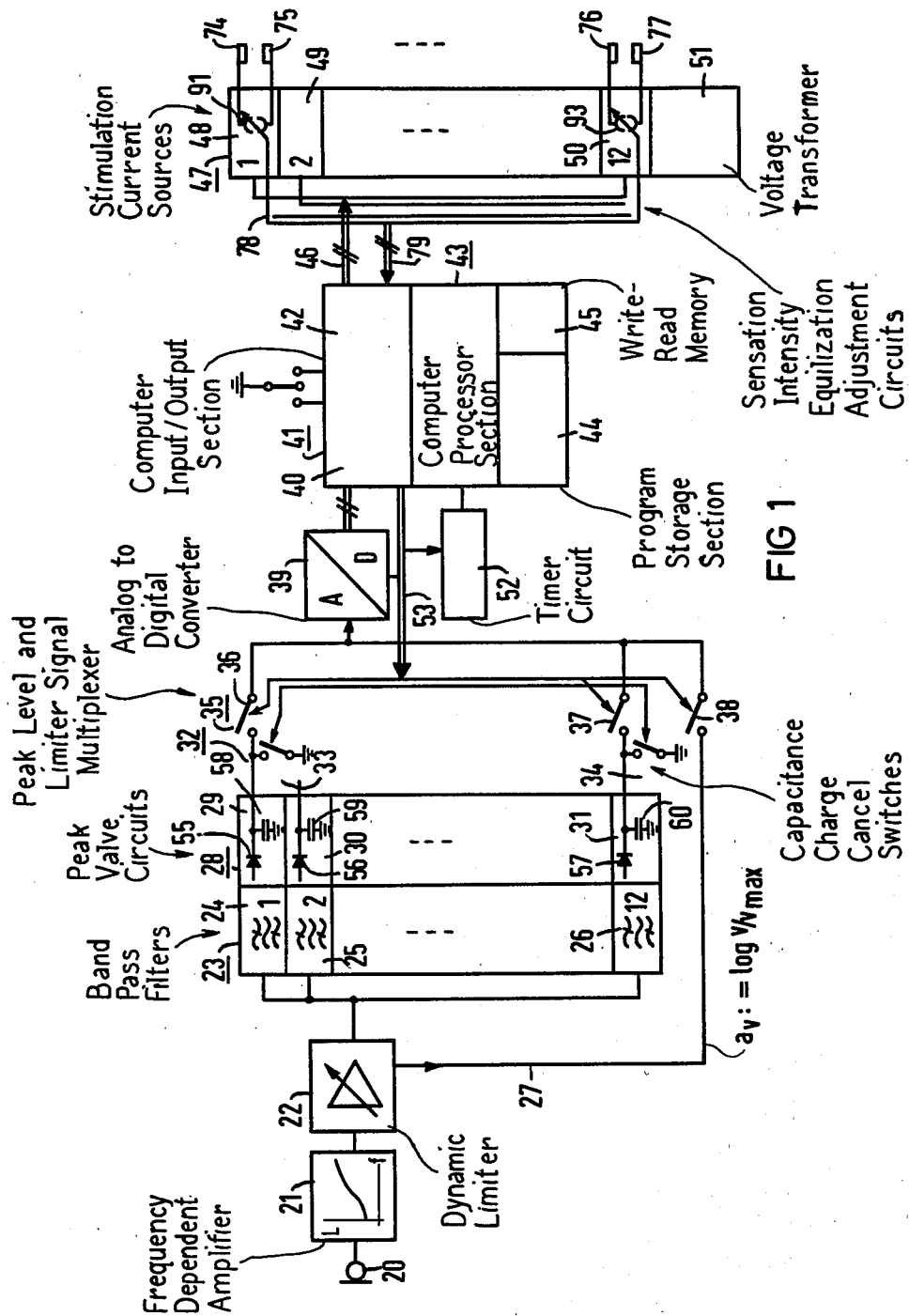
In FIG. 1 the block circuit diagram of a hearing prothesis is illustrated in which an apparatus for carrying out the method according to the invention is employed.

In FIG. 1, 20 designates a microphone which is connected to a frequency-dependent amplifier 21 which is followed by a dynamic sound volume limiter 22. The output of limiter 22 is connected to an arrangement 23 of twelve band pass filters of which those designated by 24 through 26 are individually delineated. Moreover, it exhibits a connection line 27 to the multiplexer 35. Following the band pass filter arrangement 23 is an arrangement 28 consisting of peak voltage formation-elements, of which those referenced with 29 through 31 are illustrated. Following this is a cancel switch arrangement 32, of which those which are referenced by 33 and 34 have been delineated. Following the arrangement of the cancel switches is a multiplexer 35 which, in the illustrated steps, is indicated in the form of switches 36, 37 and 38, which serves the purpose of multiplex transmission of the components generated in the band pass filter arrangement 23 to an analog-to-digital converter 39. This is then followed, via an 8-channel data bus, by the input section 40 of the computer 41. The data bus is, moreover, characterized by eight channels on account of the word size of eight bits. The computer also additionally contains an output section 42, a processor 43, a program section 44 with a capacity of 512 words, and a data section (write-read-memory) 45 with a capacity of 64 words.

Via a connection 46, which consists of twelve lines and is therefore characterized by twelve channels, the connection of the computer output section 42 with a current source arrangement 47 takes place, of which those referenced by 48 through 50 are specifically delineated as examples. They serve the purpose of generating the currents to be transmitted to the skin. Moreover, there is additionally connected with the current sources 47 a voltage transformer 51 which is designed for 120 V. A timer 52 is additionally connected to the processor section 43 of the computer 41. The latter timer serves the purpose of measuring the time intervals $T_P$ between the current pulses. The multiplexer 35 receives its control signals from the output section 42 of the computer 41 via a connection 53.

The sound signals received at the microphone 20 are amplified in the amplifier 21 such that the high frequency spectral components are raised in relation to the low frequency spectral components with the object of achieving a compensation of the level drop of averaged spectra of speech sound. Subsequently, the signal is adjusted in the dynamic sound volume limiter 22 to such a voltage level that the filter arrangement 23 is not overdriven. Simultaneously, the limiter generates a signal which represents a measure of the amplification resulting (or being adjusted) and which is supplied via the line 27 to the analog-to-digital converter 39 for further processing. In the band pass filter arrangement 23, the signals from the sound volume limiter 22 are separated into component signals corresponding to the adjustment of the band pass filters such as 24 through 26.

Figure 2:
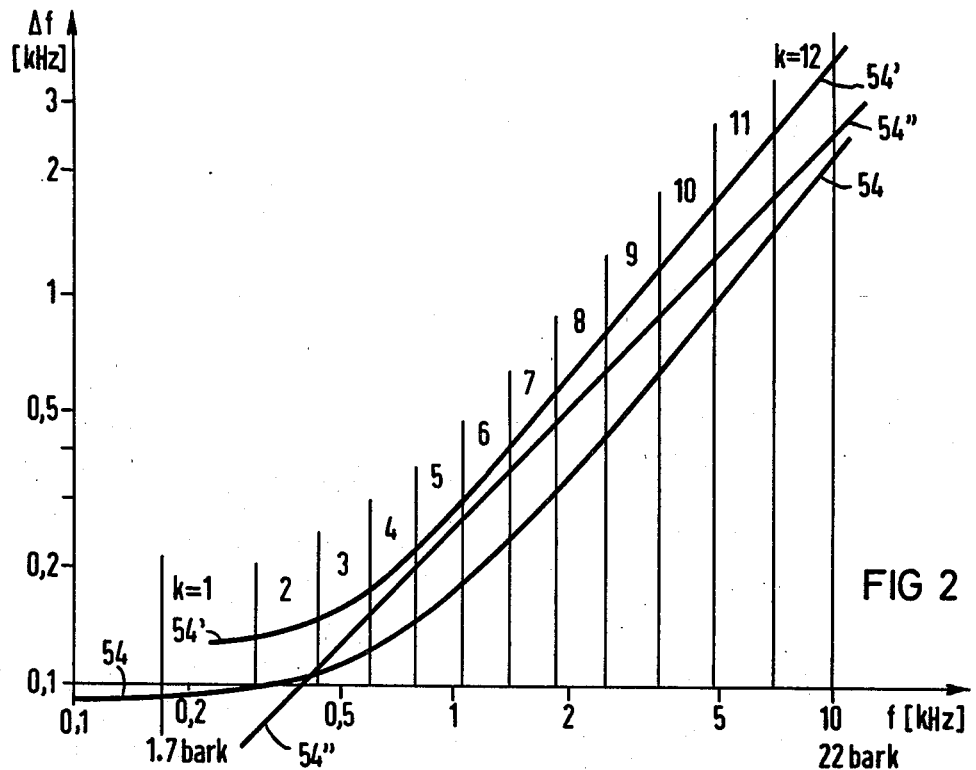
In FIG. 2 the frequency band subdivision of the band filter set employed in the case of an apparatus according to FIG. 1 is illustrated.

The spectral division of the band pass filters such as 24 through 26 is conducted in such a fashion that, in the case of a limited outlay of filter channels, in the present example, twelve different speech sounds, particularly the vowels, lead to amplitude-channel patterns which can be distinguished from one another as well as possible; i.e., lead to different amplitude-channel patterns. To this end it is expedient, on formant charts of the language to be transmitted, in the present instance, German vowels (representation of the first and second formant in the plane which is established by the two formant frequencies), to draw-in a frequency range subdivision which just barely separates from one another similar vowels, such as e.g. /u, o/ or /e, i/; i.e., limited (or restricted) frequency ranges have approximately the same width as the frequency ranges of these vowels. The frequency range magnitudes associated with these vowel boundaries were plotted in a diagram with logarithmic scale on both axes as a function of the mean frequency of the ranges in FIG. 2. These values lie approximately on a curve 54' which is similar to the progression 54 of the frequency group width. The frequency group band width is a measure of the frequency resolution capability of hearing and hence a meaningful approximation for the precision of the frequency resolution of a hearing prosthesis.

The band widths obtained from the formant chart are approximated by the curve 54' which lies above the progression 54 of $\Delta f_G$, by a factor 1.4 to 1.8. The curve 54' forms the basis for the subdivision of the frequency range important for speech into the band widths $\Delta f$ of the band pass filters. This subdivision was so effected that $\Delta f$ values plotted versus the mean frequencies f, lie on the mentioned curve 54'. In this manner, in the case of utilization of twelve band filters, selected in the present example, the frequency range of 170 Hz to 10,000 Hz is covered. The resulting band widths, for f greater than 500 Hz, are somewhat greater than the third (musical term) band widths 54'' and, for f smaller than 500 Hz, deviate therefrom in that they swing into a progression independent of f with the object of attaining a constant band width of approximately 130 Hz (the two low frequency filters, which, in the present Figure, are referenced with 24 and 25).

Figure 3:
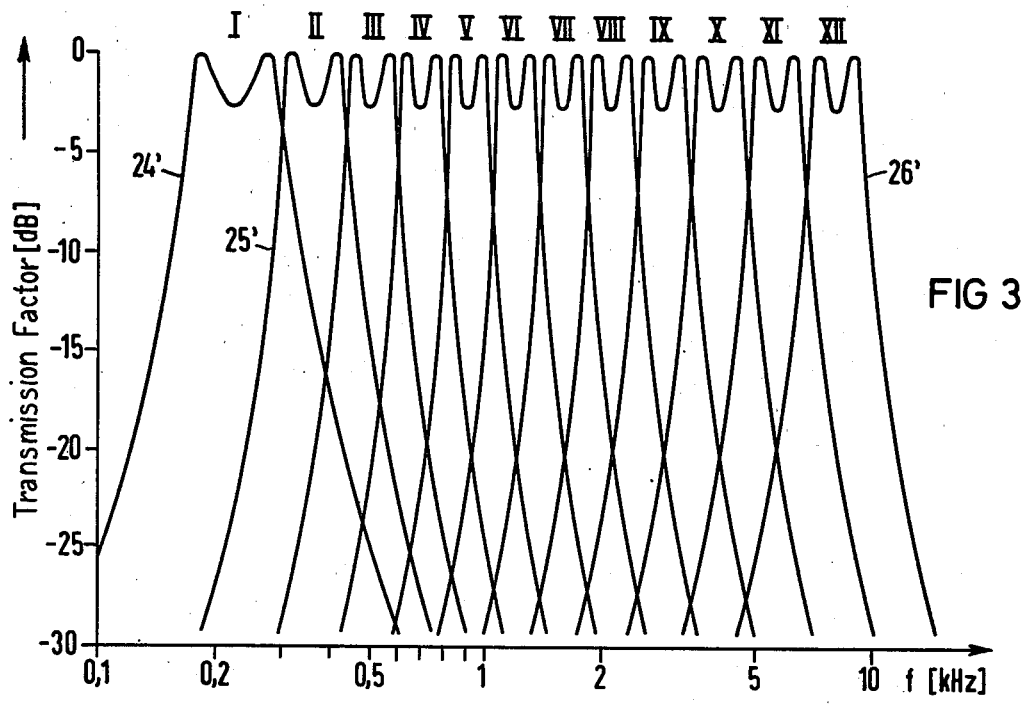
In FIG. 3 the frequency responses of the band pass filters are illustrated in a diagram in which the transmission factor is plotted relative to the frequency.

In the present example the filters are realized in the form of band pass filters such as 24 through 26 of the degree four; i.e., with an edge (or slope) rise far removed from the pass band of ±12 db/octave. They are so dimensioned that, with a minimum outlay (degree four), as high as possible an adjacent channel selectivity results. In the pass band a ripple of 3 dB was admitted. The attenuation at the frequencies at the intersection of the attenuation curves amounts to 3 to 6 dB, so that no large gaps result during the analysis of the speech frequency range. At the mean frequencies of the adjacent filters it amounts to 15 to 20 dB in order to achieve as high as possible an adjacent channel selectivity. The progressions (or curves) of the transmission factors for the individual filters are apparent from FIG. 3 (curves 24', 25', etc., to 26').

Following the band pass filter arrangement 23, half-wave rectifiers, of which those designated by 55 through 57 are schematically illustrated, and input capacitors, of which those referenced by 58 through 60 are visible—the preceding all being arranged in the peak voltage formation elements 28-form, in time segments $T_a$, the maximum values of the filter output signals. These stored values are supplied from the analog-to-digital converter 39 with the multiplexer 35, for the purpose of further processing, to the computer 41, and subsequently, in utilizing cancel switches 32, which are associated with every band filter channel, of which those are visible in FIG. 1 which are referenced with 33 and 34, said stored values are cancelled. With the commencement of the next time interval $T_a$ new maximum values can then be formed.

This method of amplitude sampling has considerable advantages precisely for speech signals, as compared with low pass filter smoothing of the rectified component signals, for the following reasons. In the case of low pass filtering, the cut-off frequency $f_g$ of the low pass filter must be placed so low that the fluctuations of the envelope curve of the filter signals (which can have frequencies of 80 to 600 Hz in the case of voiced sounds) are largely smoothed (or filtered free of ripple) in order to avoid beat effects with the sampling frequency $1/T_a$. On the other hand, it is desirable to select the rise time of the low pass filter signals to be as low as possible in order that rapid brief events (explosive sounds) are not impermissibly obliterated. Both demands contradict one another so that, as a compromise solution, one generally selects $f_g$ at 25 Hz to 50 Hz. This compromise is not necessary in the case of the inventive solution (maximum value formation and subsequent cancelling), because the maximum values are not influenced by the periodic fluctuations of the envelope curve in the rhythm of the vocal chord fundamental frequency. One need merely select $T_a$ such that $T_a$ is greater than the maximally occurring fundamental frequency period; i.e., that $T_a$ is greater than or equal to 10 ms, and what is achieved thereby is that at least one maximum of the envelope curve falls in the sampling interval $T_a$. This maximum is then independent of the frequency and phase position (or relationship) of the fundamental frequency.

In order to design the further signal processing to be as flexible as possible, it is carried out with the aid of a computer 41. An analog-to-digital converter 39 makes available the twelve channel voltages as well as the value of the attenuation constant $a_v$ of the sound volume limiter 22 to the input section 40 of the computer. The further processing steps are determined from the stored program and consist in the formation of levels from the component signals, a selection increase through suppression of weaker channels (level drop), the reproduction of the levels in the form of pulse durations with volume compression, the generation of pulses in the interval of $T_P = 5$ ms. The thus-processed signal is then supplied to the current sources of the arrangement 47, FIG. 1.

The steps of the computer require a representation of the amplitudes of the component signals as levels. Therefore, the levels $L_k$ are formed from the amplitude values through utilization of a fixedly stored table. In this table, also nonlinearities of rectification and AD-conversion can be taken into account. The component sound pressure level $L_{pk}$—present at the microphone—in the frequency band k results through simple addition of $L_k$ and $a_v$.

The next step takes into account properties of information transmission via the skin. Through the latter the flow of information is strongly restricted by virtue of the fact that the receiver (the deaf individual) is unable to process many simultaneous stimuli as well as one or two. Corresponding investigations found that the loss of information strongly increases with the number of simultaneous stimuli. Therefore, only a few stimuli, but those which are as relevant as possible (information-bearing), should be offered.

This leads to the demand for a selection of the information in which irrelevant information is suppressed in favor of relevant information. A measure of this can be the regions of local spectral maxima of the energy (formants). In this sense, from the twelve component levels $L_{pk}$ employed in the present example, those are selected those which have a maximum value relative to their surroundings (along the channel number k, or the frequency axis, respectively). This occurs through a comparison of the $K_{pk}$'s with a variable threshold $M_k$, which is defined as the arithmetic mean value of five adjacent $L_{pk}$'s.

$$M_k = \frac{1}{5} \sum_{j=k-2}^{k+2} L_{pj} (k = 1 \ldots 12). \tag{1}$$

For $j < 1$ and $j > 12$, substitute component levels can be defined which are generated from a mirror-inverted extension of the spectrum beyond its boundaries $k = 1$ or $k = 12$, respectively; thus $$L_{pj} = L_{p(24-j)} \text{ for } j > 12 \text{ and } L_{pj} = L_{p(2-j)} \text{ for } j < 1. \tag{2}$$

The number of five values for the averaging in the case of a total of twelve frequency bands, as compared with three or seven values, is to be given preference, because then the relevant energy maxima are best separated from the remaining irrelevant spectral components, as has been shown from comparative investigations of vowel spectra. The comparison $M_k$ leads to the maintenance of the component levels $$L'_{pk} = L_{pk}, \text{ if } L_{pk} \geq M_k + S, \tag{3}$$

whereby S is a threshold displacement (or shift) in the range of zero to 6 dB; in particular, 3 dB. The comparison leads to the reduction of the component levels $$L'_{pk} = L_{pk} - c(M_k + S - L_{pk}), \text{ if } L_{pk} < M_k + S, \tag{4}$$

whereby c is a factor which decides regarding the degree (or extent) of the dropping (or decrease) of the levels and can assume values of between two and twenty; in particular, ten.

A second decision leads, through a complete suppression of the contents of channel k, to the simplification, in case $$c(M_k + S - L_{pk}) \tag{5}$$

becomes greater than 20 dB.

Figure 4:
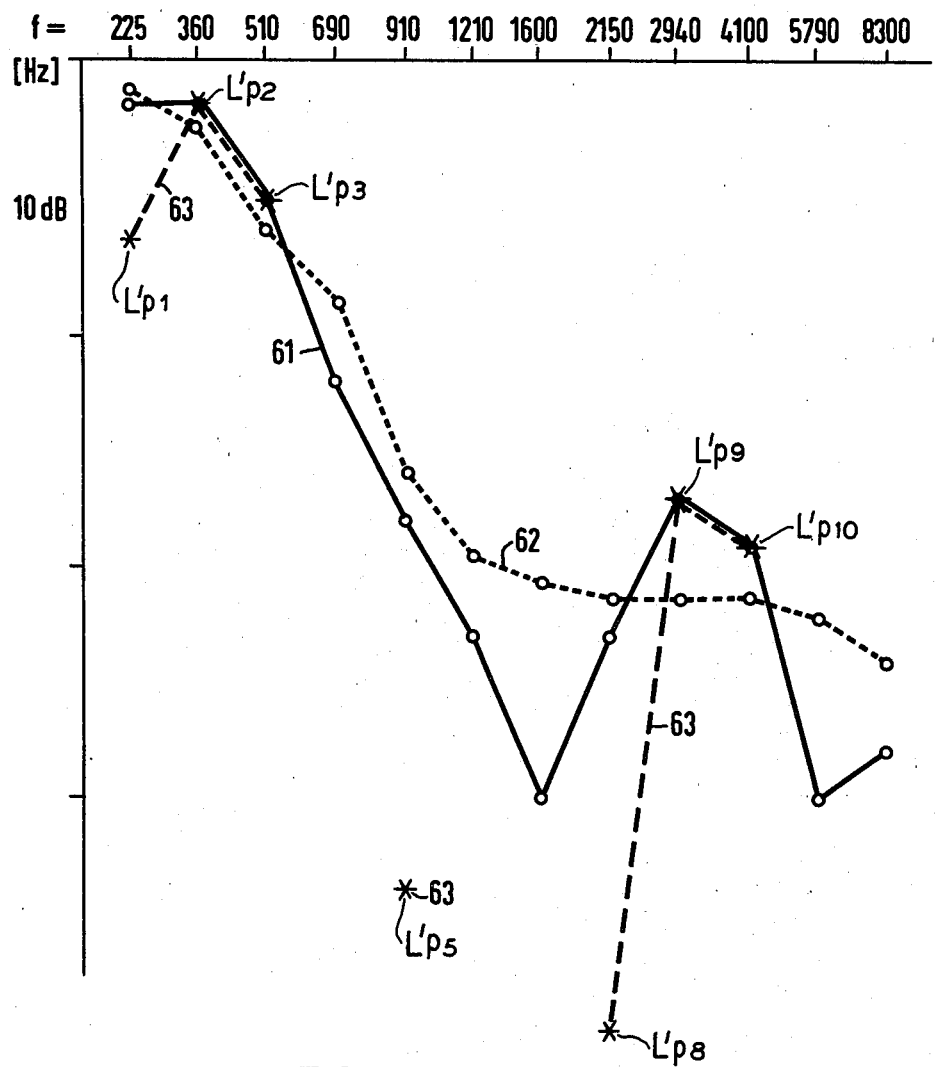
In FIG. 4 there is illustrated, in a diagram, on the example of a short-time spectrum, the method of operation of the selectivity increase in accordance with the invention, in which the component levels prior to and after the information reduction are plotted relative to the frequency.

$L'_{pk}$ then assumes a special value; i.e., the value zero, which, during the following coding of the $L'_{pk}$'s into current pulses, leads to the result that the pulse at the electrode k is omitted (or skipped). In FIG. 4, on the example of a short-time spectrum for the vowel /o/, the method of operation of this selectivity increase is illustrated in that the curve 61 illustrates the component levels $L_{pk}$ prior to the level drop (or decrease); curve 62 represents the threshold values $M_k + S$, and curve 63 represents the component levels $L'_{pk}$ after the level drop. It is more intense the greater the values S and c. The remaining levels $L'_{pk}$ represent an "emaciated" version of the short-term spectrum, determined in the interval $T_a$, in which levels the most important information for the discrimination of different speech sounds, namely the progression of the levels in the frequency ranges of the formants, has remained. This information core (or nucleus) is now employed in order to control the pulses of the current which are transmitted for application to the patient on electrodes of the arrangement, of which those referenced with 74 through 77 are shown in FIG. 1. The patient thus perceives sensory patterns which are correlated as well as possible with different speech events.

Numerous investigations of a psychophysical nature form the basis for this step; i.e., the reactions of test individuals to pulse-shaped current stimuli of different types with variation of the describing parameters were evaluated (or analyzed). For electric stimulation on the skin surface, for the purpose of (in the sense of speech information) the rapid transmission of information, a specific type of time dependency of the current at several electrodes has proven expedient. This is apparent from FIG. 5 in that, with the plotting of the current i relative to the time t, in the curves 64 to 67, at the curve 64 in the channel k=1, the present current intensity results to a rectangular pulse 68 of the duration $T_{i1}$ which, according to the corresponding development of the curve at 69, after a time of $T_p$, repeates itself. It is similar in the case of curve 65 for the channel k=2 in which, for the duration of $T_{i2}$, a rectangular pulse 70 results which is followed immediately thereafter by an exponentially decaying reverse current pulse 70' with the duration $T_{e2}$. This reverse current, insofar as it has not completely decayed in $T_{e2}$, can be interrupted for the duration $T_{i3}$ of the rectangular pulse in the next channel k=3 (70''). $T_e$ lies between 100 µs and 200 µs. Also the progression 70 is repeated as 71, as the pulse 68 of curve 64 is repeated as 69. In curve 66 there likewise results, with an interval of $T_{e2}$ from the lower tip (or peak) of 70, a progression for $T_{i3}$ which is referenced with 72. This is then continued to the curve 67 for the channel k=12 in which the progression of the pulse with the duration $T_{i12}$ results at 73. The current appearing at the electrodes such as 74 through 77 must satisfy the following conditions (or prerequisites):

1. The long time integral of the current (DC current mean value) must be zero in order that no damage to the skin result due to DC current, i.e.

$$\lim_{T \to \infty} \frac{1}{T} \int_T i(t)\, dt = 0 \tag{6}$$

This is achieved by means of a current return flow which, for the most part, occurs immediately after the rectangular stimulation current pulse in the discharge time intervals $T_{ek}$. These exponentially decreasing reverse currents result due to discharge of the capcitance $C_{E1}$, which is a part of the electrode impedance $\underline{Z}_{E1}$, which is generated by the properties of the skin tissue disposed beneath the electrodes such as 74 to 77.

Figure 7:
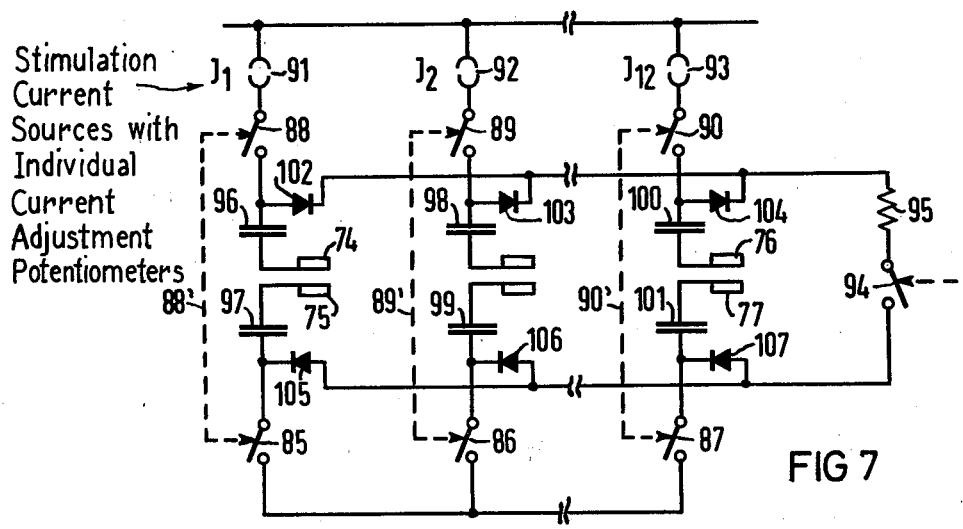
In FIG. 7 a section of a circuit is illustrated in which the currents to be transmitted to the electrodes are generated.

($\underline{Z}_{E1}$ can be, roughly simplified, represented as a parallel connection of the capacitance $C_{E1}$ with the resistance $R_{E1}$). The discharge proceeds via the discharge diodes such as 102 to 107 (see FIG. 7) and a discharge circuit consisting of $R_e$ (95) and $S_e$ (94) which is common to all current sources. A smaller portion of the discharge takes place following the sequence of stimulation- and discharge-intervals.

$$T_{ik} + T_{ek} \text{ (k=1 through 11)} \tag{7}$$

namely, in the relatively long discharge time segment $T_{e12}$. The observance of the cited demand for DC current-free stimulation is guaranteed by the blocking (or isolating) capacitors C (96-101).

2. The current stimuli are to bring about the following sensations which (a) are pain-free and not unpleasant to as great an extent as possible;

(b) are as similar as possible to the sensations which are produced by periodic mechanical stimuli (vibrations); i.e., the unmodulated electrocutaneous sensations are to possess as little as possible a self- (or inherent) time structure (comparable to the acoustic sensation in the case of an unmodulated sine tone), in order to be "free" for the characteristic modulations by the speech signal. Thus, no "rough" sensations, such as prickling sensations or the like, should result;

(c) possess as small as possible a local spread (along the skin surface), in order that they will not overlap with sensory ranges of the adjacent electrodes and lead to confusion;

(d) can follow chronologically, in as inertia-free manner as possible, the modulations of the speech signal in order that the time structure of the speech signal can be transmitted as well as possible to the time structure of the sensation;

(e) do not mutually influence one another in the case of a plurality of simultaneously occurring sensations (at different locations); i.e., the component sensation at the location k is not to be dependent upon the current stimulus at the location j≠k;

(f) are largely independent of variations of the electric resistance of the skin;

(g) attain a mean, well-perceptible intensity with as little stimulation energy as possible.

These demands are largely met by a special time progression of the current in the manner specified in the following.

(a) The current intensity i(t), during the stimulation current interval $T_i$, is constant and independent of the skin resistance $Z_{E1}$; i.e., the current is impressed in the form of a rectangular pulse. The internal resistance $R_i$ of the current source is much greater than $\underline{Z}_{E1}$ (e.g. $R_i = 1$ MΩ, if $Z_{E1} = 10$ kΩ).

Figure 5:
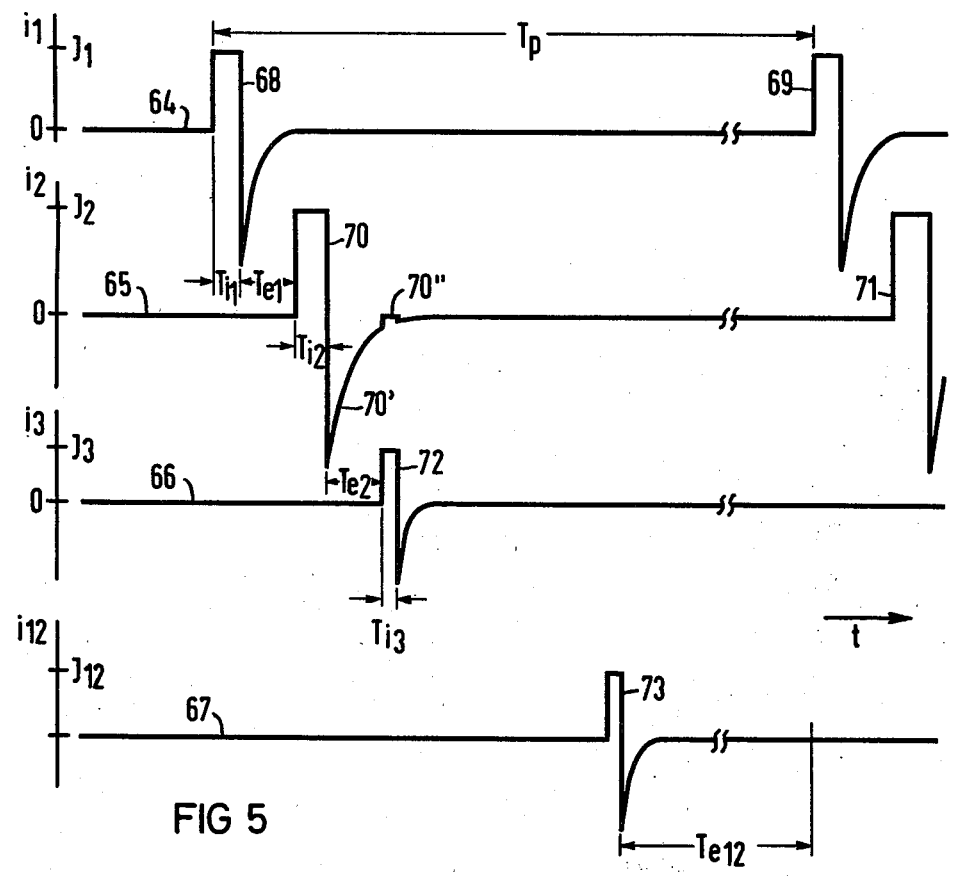
In FIG. 5 the time dependency of the current at a plurality of electrodes is illustrated.

(b) The stimulation current intervals $T_{ik}$ at different electrodes cannot be permitted to chronologically overlap one another in order that the currents at the electrode parts, which are connected to the common zero volt line during $T_i$, do not mutually influence one another. This necessitates a sequential generation of the stimulation currents in an arrangement such as is illustrated in FIG. 5.

(c) The stimulation current times $T_i$ are to be ($T_{ik}$) smaller than or equal to 100 µs.

(d) Immediately following the stimulation current time interval $T_{ik}$ is a reverse current time interval $T_{ek}$ with $T_{ek}$ greater than 100 µs in order that the effect of the stimulation current energy is only brief (or short-term).

(e) The stimulation repetition period $T_p$ lies in the range of 4 ms to 10 ms (in the present example $T_p = 4$ to 5 ms has been shown to be optimum). This corresponds to a maximum sensitivity for mechanical vibrations at approximately 200 Hz.

This dimensioning of the time progressions implies for mean sensation intensities, stimulation current intensities $I_k$ in the range between 2 mA and 10 mA, for which the current sources must be designed.

Figure 6:
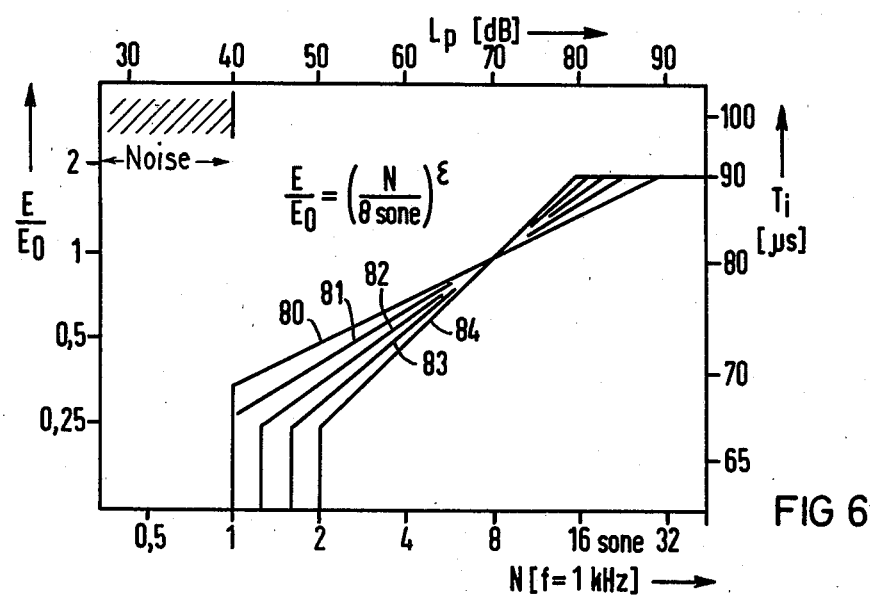
In FIG. 6 the allocation of the sound pressure levels to the sensitivity intensity and pulse duration is indicated.

The sensation intensity E, for $T_i < 100$ μs is dependent, in a good approximation, upon the stimulation parameters I, $T_i$ through a function $$E = f(I \cdot T_i) \quad (8)$$

i.e., upon the charge which flowed during $T_i$. Resulting therefrom, as an optional approximation function for the relation between E and $T_i$ from FIG. 6 is $$E \approx E_o \left(\frac{T_i}{T_o}\right)^{m(T_i)} \text{ with } m(T_i) = m_o \left(\frac{T_i}{T_o}\right)^{-2.5} \quad (a)$$

with I = const. ($T_o$ and $m_o$ are constant reference magnitudes). Thus, in order to control E, it is possible to modulate I as well as $T_i$. Specifically for operation by means of a process control computer, the modulation of the pulse duration; i.e., of the $T_i$, is less costly than that of the current intensity, because, in the first instance, no conversion from digital to analog values is necessary, which would be the case in the latter instance.

In addition, there is the fact that, on account of the varying sensitivity of different skin locations, the charges $I \cdot T_i$ differ from one another for the same sensation intensity E. This can be taken into account in that the values $I_k \cdot T_{ik}$, at the twelve locations of the skin, are adjusted for the equal (mean) E's; for example, with twelve adjustment (or setting) controls. Proceeding from these adjusted fundamental values $I_{ok} \cdot T_{iok}$, the spectral values $L'_{pk}$ can now effect a modulation.

From a technical point of view it is advisable to adjust the current intensities $I_k$ with potentiometers (in the case of reference-pulse durations $T_{io}$) to the same (or equal) $E_k = E_o$ (mode of operation: adjustment) and to control the $I_k \cdot T_{ik}$, and hence the $E_k$ through modulation of the $T_{ik}$ (normal mode of operation).

In order, in the case of the mode of operation "adjustment", to avoid the necessity of applying twelve switches and nevertheless be able to connect the reference signal to the respective electrode k, the adjustment button of the respective potentiometer can be equipped with an additional "sensor function", referenced in FIG. 1 with 78. By this means, through mere contacting of the adjustment button (or knob), the respective channel k is subjected to the reference-adjustment signal. Through the arrow 79 the reaction on the computer 41 is indicated.

The modulation of the $T_{ik}$ assumes that the relation between sensation intensity E and $T_{ik}$ is known and that one has made an assumption regarding the best allocation between E and the sound level $L'_p$. The simplest type of such an allocation, analogously to the psycho-acoustics of sound hearing, is the dependency $$\frac{E}{E_o} = \frac{N}{N_o} = 2^{\frac{L_p - L_{po}}{10 \text{ dB}}} \text{ (for } L_p > 40 \text{ dB} = L_{po}) \quad (9)$$

with the loudness N (reference value $N_o$). This signifies that the sensation intensity E, with increasing level, runs proportionally to N and that E varies by the factor eight in the level range between 50 and 80 dB (range of the sound intensity of normal conversation).

The range of sensation usable for electrocutaneous stimuli is very restricted and the function $$E = f(I \cdot T_i) \quad (10)$$

is strongly dependent upon the location on the skin where the electrode is applied. Therefore, it is expedient to select an allocation $E = f_E(L_p)$ wherein E is more weakly dependent upon $L_p$ than disclosed above in equation (9). Therefore, the general relation $$\frac{E}{E_o} = \left(\frac{N}{N_o}\right)^\epsilon = 2^{\frac{L_p - L_{po}}{10 \text{ dB}} \cdot \epsilon} \quad (11)$$

is introduced with an $\epsilon$-designated exponent of altogether 0.4 to 1. It comprises, for $\epsilon$ smaller than 1, a compression of the dynamic sound volume range contained in the sound signal.

For example, for $\epsilon = 0.5$, there corresponds to a loudness ratio of 1:4 a sensation intensity ratio of 1:2. The optimum value for $\epsilon$ was experimentally determined to be approximately 0.6 during the transmission of speech. In FIG. 6 the relation between $L_p$, N, E and $T_i$, for five different values of $\epsilon$ is illustrated. During plotting in a diagram straight lines 80 through 84 result for all five values, which, however, have a different inclination. For $\epsilon = 0.5$, they are referenced with an 80; for $\epsilon = 0.625$ with 81; for $\epsilon = 0.75$ with 82; for $\epsilon = 0.875$ with 83; and for $\epsilon = 1$ with 84. That the straight line which is referenced with 81 and stands for $\epsilon$ approximated to 0.6 corresponds to an optimum is apparent from the cited experiment (during the transmission of speech).

For the method underlying the invention, only the function $T_i(L_p)$ is important, which is available in the computer in the form of a table and hence demands little computer time. It is also additionally possible to incorporate in this table an upper limit on the generated sensation intensity E. Exposing the receiver to unnecessarily high sensation intensities is thereby avoided.

Upon falling below a threshold of the sound level of 40 to 50 dB, which can, for example, already be provided by a noise level, stimulation pulses are entirely suppressed by correspondingly applying the table. Thus, stimulation pulses are avoided which are irrelevant because they contain no information from the speech sound to be transmitted. Moreover, the disturbance (or interference) not pertaining to speech is eliminated.

With the thus-ascertained (or determined) value for $T_i$, the computer generates a switching pulse in the respective channel k which controls the switches $S^o_k$, which are referenced with 85 through 87; $S^+_k$, which are referenced with 88 through 90 (FIG. 7), so that, in conjunction with the current $I_k$ adjusted by means of potentiometers (contained in the current sources 91 through 93), the charge $I_k \cdot T_{ik}$ is displaced (or shifted). The broken lines 88', 89' and 90' here signify that $S^o_k$ and $S^+{}_k$ are simultaneously actuated, respectively. Immediately after opening of the switches 85 to 90, through $S_e$, a switch 94 is closed for the time $T_{ek}$ via a resistance 95, which effects the above-cited reverse current. In the current source circuit 47 (FIG. 1) there are additionally contained the blocking capacitors such as 96 to 101, as well as decoupling diodes such as 102 to 104, directed (or aligned) in the direction of increasing number of k, as well as oppositely directed diodes 105 to 107.

Figure 8:
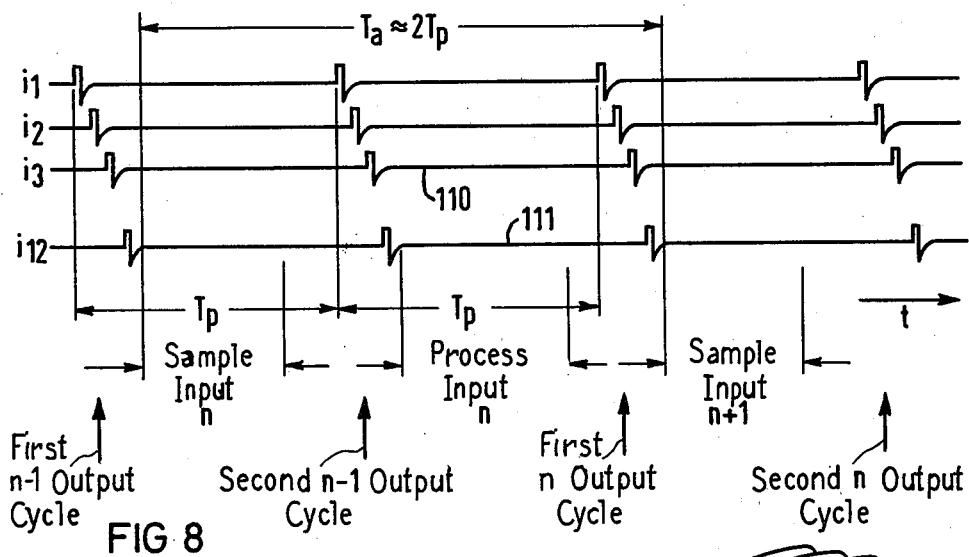
In FIG. 8 the distribution of the computer time between the different tasks of the computer is indicated; and In FIG. 9 the arrangement of the electrodes on the skin of a deaf individual is illustrated.

In FIG. 8, the division of the computing time is graphed. The different tasks, respectively, are here taken into account. The plotting of the current progression over time yields curves 108, 109, 110 and 111 of similar routes of lines as the curves 64 through 67 according to FIG. 5. The current flow times follow one another with the frequency $1/T_p$ of approximately 200 Hz. Since, for the sampling rate of the channel amplitudes, the requirement $1/T_a$ equal to or small than 100 Hz was set up and since, in the interest of a detection also of rapid spectral variations, $1/T_a = 100$ Hz is selected, the illustrated overlapping of two stimulation current periods per sampling period results.

After the current flow times there follows alternately the sampling of the channel amplitudes, or of the calculation of the dropped levels, respectively. Only then can the sampled values develop into (or take effect as) stimulation patterns. There thus results, between the scanning (or sampling) of the spectrum and the second output of the respective stimulation pattern, a maximum delay time of 3 $T_p$ amounting to approximately 15 ms which is justifiable from a cybernetic point of view because this short time-span is irrelevant for the reception of foreign speech signals as well as for the perception of one's own language. Disturbances due to a delay between speaking and hearing that which is spoken occur only for times which are greater than 50 ms.

Finally, in the case of the division into twelve information components selected in the present example, the stimulation currents are supplied via twelve twin wire cables to the electrode arrangement including electrodes such as 74 through 77 (FIG. 1). The latter can assume the most diverse forms, in the form of the electrode itself (concentric or rectangular), in the pole number (as a bipolar electrode pair 74, 75 and 76, 77, corresponding to FIG. 1, or also as unipolar electrodes with an "indifferent" return electrode common to all twelve channels), and in the arrangement of the electrodes over the skin surface.

As favorable body parts for the transmission of signals, as in the case of known arrangements, the arms were selected. In the case of the latter, a compromise results from the demands of neurophysiology (on account of the favorable reproduction conditions on central-nervous projection areas, the fingers would be best suited) and from practical considerations (the fingers should remain as free as possible for the tasks of daily life and the hearing prosthesis should be capable of being worn as often and as long as possible).

Figure 9:
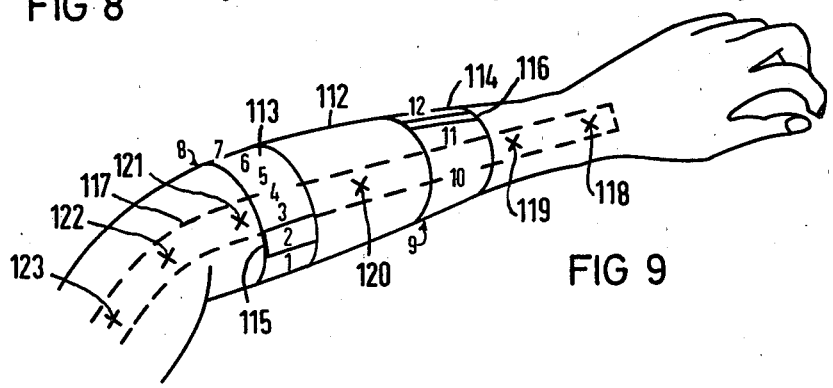
FIG. 9A shows an arrangement of electrodes wherein sets of electrodes are disposed on both of the arms.

Psychophysical recognitions speak in favor of the fact that channels with successive mean frequencies should be allocated to adjacent positions in the direction perpendicular to the longitudinal axis of the respective arm. In exchange for this, the danger of confusion of adjacent electrodes is less than in the case of an arrangement along the length of the arm axis. Adjacent electrodes here lie on a ring around the arm. In view of the necessary contact surfaces, it is not possible for reasons of space to accommodate all twelve electrodes of the present example on one single such ring. The electrodes are therefore divided over several rings in a known fashion. This leads to an arrangement which is expedient according to the concept of the invention in which, as is apparent from FIG. 9, a ring 113 with eight electrodes 1 through 8 which are associated with the low frequency channels, is near the elbow of the forearm 112. A second ring 114 comprising four electrodes 9 through 12 for the high frequency channels lies in proximity to the wrist. This distribution is selected because the arm circumference in proximity to the elbow is greater than at the wrist and can correspondingly accommodate more electrodes.

The electrode poles are manufactured from inert electrically conductive material in relation to the contacted skin. On account of the low manufacturing costs, the utilization of rectangular strips of thin rust-free (or stainless) steel sheet material with edge dimensions of $l_1$, $l_2$, with approximately $l_1 = 5$ to 10 mm and $l_2 = 10$ to 20 mm has proven successful. An electrode surface of 1 cm$^2$ to B 2 cm$^2$ is recommendable in order than enough nerve fibers are detected. The width $l_3$ of the gap between the poles lies favorably for $l_3 = 1$ to 3 mm. The strips are applied on flexible elastic supports, for example, consisting of rubber, which, in turn, are secured on a band of expandable material. At the ends of the bands 113 and 114, each of which is to be simply wound about the arm, "self sticking closures" 115 and 116 are secured. In this fashion, the bands can be easily and rapidly closed and opened again, respectively.

Figure 9A:
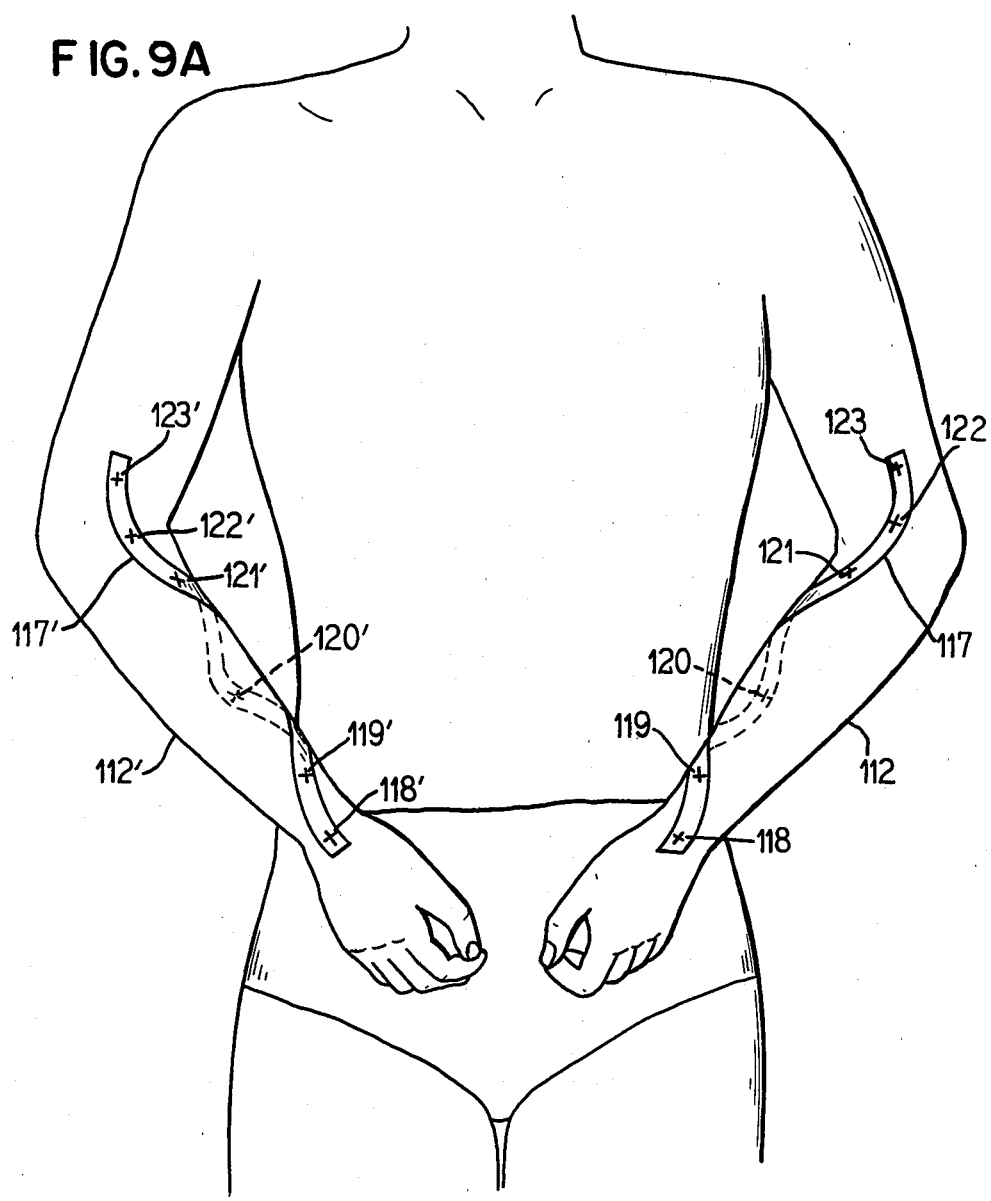

FIG. 9A illustrates the case wherein about twelve electrodes are applied with about six electrodes arranged on the left arm and about six electrodes arranged on the right arm.

The arrangement of the electrodes can also be distributed over more than two rings. Thus, e.g. over four rings with three electrodes each which are worn on the left and on the right forearm and upper arm. The electrodes can then be further removed from one another and can reach a greater central-nervous projection area. In the same sense, the electrodes can also be arranged along the length of a line, indicated in broken lines as band 117 in FIG. 9. The band 117, FIGS. 9 and 9A runs from the left wrist to the left shoulder (six electrodes 118 to 123 on the left arm) and as indicated in FIG. 9A, a further band 117' extends from the right shoulder to the right wrist (six electrodes 118' to 123' on the right arm). The bands 117 and 117' here change arm sides (from the exterior toward the interior and back), in order that the different positions in the direction of the circumferential line of the arm; i.e., perpendicular to the longitudinal axis, set up an additional, well-perceptible local dimension.

The experiments conducted with a system constructed in accordance with the invention have shown that test individuals already after a practice time of approximately ten to fifteen hours, are able to correctly recognize monosyllabic words with a reliability of 90 to 95%, without, in addition to the electric stimuli, other information channels, such as optical reading-off from the lips, having been utilized.

It will be apparent that many modifications and variations may be effected without departing from the scope of the novel concepts and teachings of the present invention.

Definitions of the frequency resolution capability and frequency group width are described in the publication "Subdivision of the Audible Frequency Range into Critical Bands (Frequenzgruppen)" of E. Zwicker in "The Journal of the Acoustical Society of America" Volume 33, Number 2, February 1961. According to this publication "The subdivision of the frequency range over which the human ear is able to perceive tones and noises is often desirable for the handling of various problems. For mathematical and physical purposes it is useful to divide the scale either linearly or geometrically (logarithmically) as, for example, into octave and third-octave bands. Some problems, on the other hand, call for a subdivision more closely related to the manner in which the ear itself appears to carry out the process. Here the subdivision into critical bands seems to be very useful. These bands have been directly measured in experiments on the threshold for complex sounds, on masking, on the perception of phase, and most often on the loudness of complex sounds. In all these phenomena, the critical band seems to play an important role. It must be pointed out that the measurements taken so far indicate that the critical bands have a certain width, but that their position on the frequency scale is not fixed; rather, the position can be changed continuously, perhaps by the ear itself. Furthermore, the subdivision into critical bands seems to be correlated very closely to the cochlear mechanics, to frequency discrimination, and to the mel scale of pitch."

We claim as our invention:

1. A method for producing electric stimulation patterns as a function of acoustical information, which patterns can be transmitted to the skin of an individual by means of electrodes and can be interpreted as acoustical information, said method comprising converting the acoustic signals into electrical signals, separating the electrical signals into frequency bands, and transmitting stimulating signals to respective electrodes based on the information in respective frequency bands, characterized in that electric signals from an acoustic to electric transducer are separated into component signals in band pass filters of frequency band widths (curve 54', FIG. 2) substantially corresponding to the frequency resolution capability of hearing (curve 54, FIG. 2), the latter component signals then being converted into signal levels corresponding to the component signal amplitudes, and, finally, taking into account the sensation intensity per electrode and following suppression of irrelevant components, the signal levels are converted into pulse durations of current pulses which are supplied to the electrodes, wherein separation of the transducer electric signals into component signals is effected in filter channels (k=1 to 12), whose band widths have approximately the values as the frequency ranges which are occupied by vowels which are to be distinguished for one another, wherein the band widths of the band pass filter channels (curve 54', FIG. 2) lie above the frequency group width (curve 54, FIG. 2) pertaining to the mean frequency by a factor of 1.4 to 1.8, and wherein the band widths of the filter channels with mean frequencies above 500 Hz are somewhat greater than third band widths (curve 54", FIG. 2), and the band widths of filter channels with mean frequencies less than 500 Hz define a band width as a function of mean frequency which is relatively independent of the mean frequency and is approximated by a constant band width of approximately 130 Hz to 150 Hz.

2. A method for producing electric stimulation patterns as a function of acoustical information, which patterns can be transmitted to the skin of an individual by means of electrodes and can be interpreted as acoustical information, said method comprising converting the acoustic signals into electrical signals, separating the electrical signals into frequency bands, and transmitting stimulating signals to respective electrodes based on the information in respective frequency bands, characterized in that electric signals from an acoustic to electric transducer are separated into component signals in band pass filters of frequency band widths (curve 54', FIG. 2) substantially corresponding to the frequency resolution capability of hearing (curve 54, FIG. 2), the latter component signals then being converted into signal levels corresponding to the component signal amplitudes, and, finally, taking into account the sensation intensity per electrode and following suppression of irrelevant components, the signal levels are converted into pulse durations of current pulses which are supplied to the electrodes, wherein the component signals from the band pass filters are supplied to half-wave rectifiers and charging capacitors to produce said signal levels, and the signal levels are supplied, via an analog-to-digital converter (39) and a multiplexer (35), to a process control computer (41), and periodically the signal levels are erased at the capacitors, so that, in uniform time intervals ($T_a$), the maximum values of the component signals from the band pass filters are formed as said signal levels.

3. A method according to claim 2, wherein the uniform time interval $T_a$ for charging of the capacitors is greater than the maximally occurring fundamental frequency period and hence is greater than or equal to ten milliseconds.

4. A method for producing electric stimulation patterns as a function of acoustical information, which patterns can be transmitted to the skin of an individual by means of electrodes and can be interpreted as acoustical information, said method comprising converting the acoustic signals into electrical signals, separating the electrical signals into frequency bands, and transmitting stimulating signals to respective electrodes based on the information in respective frequency bands, characterized in that electric signals from an acoustic to electric transducer are separated into component signals in band pass filters of frequency band widths (curve 54', FIG. 2) substantially corresponding to the frequency resolution capability of hearing (curve 54, FIG. 2), the latter component signals then being converted into signal levels corresponding to the component signal amplitudes, and, finally, taking into account the sensation intensity per electrode and following suppression of irrelevant components, the signal levels are converted into pulse durations of current pulses which are supplied to the electrodes, wherein the conversion of the signal levels into pulse durations takes place periodically with suppression of weaker channels (level decrease), and with dynamic compression during intervals of about five milliseconds duration in a process control computer (41).

5. A method according to claim 4, wherein, in order to eliminate irrelevant information, a comparison with a threshold $M_k$ is carried out, which threshold is calculated as an arithmetic mean value of five adjacent component sound pressure levels $L_{pk}$, respectively, according to which the $L_{pk}$'s are reduced if they are smaller than $M_k+S$; namely, by the amount $c(M_k+S-L_{pk})$, wherein c is a value which lies in the range from about two to about twenty, and where S signifies a threshold displacement of up to about six decibels to provide a stronger reduction of irrelevant levels; this procedure being carried out for all present levels $L_{pk}$.

6. A method according to claim 5, wherein c has a value of about ten.

7. A method according to claim 4, characterized in that sensation intensities E are associated with the levels $L'_{pk}$ according to the relation $$\frac{E}{E_o} = 2\epsilon \cdot \frac{L'_{pk} - L_o}{10 \text{ dB}}$$

with $\epsilon = 0.4$ to 1, preferably 0.6; $E_o$ and $L_o$ being constant reference magnitudes.

8. A method for producing electric stimulation patterns as a function of acoustical information, which patterns can be transmitted to the skin of an individual by means of electrodes and can be interpreted as acoustical information, said method comprising converting the acoustic signals into electrical signals, separating the electrical signals into frequency bands, and transmitting stimulating signals to respective electrodes based on the information in respective frequency bands, characterized in that electric signals from an acoustic to electric transducer are separated into component signals in band pass filters of frequency band widths (curve 54', FIG. 2) substantially corresponding to the frequency resolution capability of hearing (curve 54, FIG. 2), the latter component signals then being converted into signal levels corresponding to the component signal amplitudes, and, finally, taking into account the sensation intensity per electrode and following suppression of irrelevant components, the signal levels are converted into pulse durations of current pulses which are supplied to the electrodes, wherein the current pulses supplied to the electrodes have a current intensity during the stimulation current interval which is constant and independent of the skin resistance by virtue of the fact that the internal resistance of the current source employed for generation of the pulses is made much greater than the skin resistance, that the stimulation current intervals do not chronologically overlap one another, that the stimulation current durations are not greater than about one hundred microseconds, that the stimulation current pulses are followed by a reverse current time segment which is longer than one hundred microseconds, and that the stimulation current pulse repetition period lies at a value in the range from about four to about ten milliseconds.

9. A method according to claim 8, with said current pulse repetition period being of a value in the range from about four to about five milliseconds.

10. A method according to claim 8, wherein the transmitted stimulation current energy is modulated in pulse duration corresponding to $$E = f(I \cdot T_i) \approx E_o \cdot \left(\frac{T_i}{T_o}\right)^{m(T_i)} \text{ with } m(T_i) \approx m_o \cdot \left(\frac{T_i}{T_o}\right)^{-2.5}$$

($T_o$ and $m_o$ being constant reference magnitudes with I=const.) wherein E is the sensation intensity, I the current and $T_i$ the duration of the current pulse.

11. A method according to claim 8, wherein an adjustment of the current intensities at all electrodes takes place to provide equal mean sensation intensities.

12. A method according to claim 11, wherein the current intensities are adjusted (with the aid of a reference signal) by potentiometers whose adjusters have a "sensor function", such that, upon actuation of the setting element, the adjustment of the respective current source automatically takes place.

13. A method according to claim 11, wherein an upper limitation of the sensation intensity is provided in order to avoid the occurrence of pain in the case of high sound levels.

14. A method for producing electric stimulation patterns as a function of acoustical information, which patterns can be transmitted to the skin of an individual by means of electrodes and can be interpreted as acoustical information, said method comprising converting the acoustic signals into electrical signals, separating the electrical signals into frequency bands, and transmitting stimulating signals to respective electrodes based on the information in respective frequency bands, characterized in that electric signals from an acoustic to electric transducer are separated into component signals in band pass filters of frequency band widths (curve 54', FIG. 2) substantially corresponding to the frequency resolution capability of hearing (curve 54, FIG. 2), the latter component signals then being converted into signal levels corresponding to the component signal amplitudes, and, finally, taking into account the sensation intensity per electrode and following suppression of irrelevant components, the signal levels are converted into pulse durations of current pulses which are supplied to the electrodes, wherein maximum values of the component signals from the band pass filters are formed as said signal levels in successive sampling intervals with a given sampling period ($T_a$), and wherein the current pulses are supplied to the electrodes during successive stimulation current intervals having a given stimulation period ($T_p$), and wherein two stimulation current periods per sampling period are provided.

15. A method for producing electric stimulation patterns as a function of acoustical information, which patterns can be transmitted to the skin of an individual by means of electrodes and can be interpreted as acoustical information, said method comprising converting the acoustic signals into electrical signals, separating the electrical signals into frequency bands, and transmitting stimulating signals to respective electrodes based on the information in respective frequency bands, characterized in that electric signals from an acoustic to electric transducer are separated into component signals in band pass filters of frequency band widths (curve 54', FIG. 2) substantially corresponding to the frequency resolution capability of hearing (curve 54, FIG. 2), the latter component signals then being converted into signal levels corresponding to the component signal amplitudes, and, finally, taking into account the sensation intensity per electrode and following suppression of irrelevant components, the signal levels are converted into pulse durations of current pulses which are supplied to the electrodes, wherein the electrodes are arranged on a band (113) disposed about the arm (112) and extending perpendicularly to the longitudinal axis of the arm (112), such that successive mean frequencies are associated with adjacent positions (1 to 8).

16. A method according to claim 15, wherein about twelve electrodes are applied with about eight electrodes arranged in a ring along the length of the band (113) which lies in proximity of the elbow of the forearm (112) and with which low frequency channels (1 through 8) are associated, and with about four further electrodes being disposed in a ring along the length of a further band (114) which is disposed about the forearm (112) in the proximity of the wrist and which is connected with the high frequency channels (9 through 12).

17. A method for producing electric stimulation patterns as a function of acoustical information, which patterns can be transmitted to the skin of an individual by means of electrodes and can be interpreted as acoustical information, said method comprising converting the acoustic signals into electrical signals, separating the electrical signals into the frequency bands, and transmitting stimulating signals to respective electrodes based on the information in respective frequency bands, characterized in that electric signals from an acoustic to electric transducer are separated into component signals in band pass filters of frequency band widths (curve 54', FIG. 2) substantially corresponding to the frequency resolution capability of hearing (curve 54, FIG. 2), the latter component signals then being converted into signal levels corresponding to the component signal amplitudes, and, finally, taking into account the sensation intensity per electrode and following suppression of irrelevant components, the signal levels are converted into pulse durations of current pulses which are supplied to the electrodes, wherein about twelve electrodes are applied with about six electrodes arranged on the left arm and about six electrodes arranged on the right arm, so that the electrodes lie in a line which rises from the left wrist to the left shoulder and leads from the right shoulder to the right wrist, with the means frequencies of the respective band filters coupled to the respective electrodes along this line increasing or decreasing in a monotonic fashion.

18. A method according to claim 16, wherein the electrodes are in the form of strips of stainless sheet steel with a shorter dimension of from about five to about ten millimeters and a longer dimension of from about ten to about twenty millimeters, the longer sides of successive strips having a spacing in the range from about one to about three millimeters.

19. A method according to claim 15 wherein the electrodes are disposed along the length of the band (113) which is formed into a ring configuration by means of a self adhesive closure (115).

20. A method for producing electric stimulation patterns as a function of acoustical information, which patterns can be transmitted to the skin of an individual by means of electrodes and can be interpreted as acoustical information, said method comprising converting the acoustic signals into electrical signals, separating the electrical signals into frequency bands, and transmitting stimulating signals to respective electrodes based on the information in respective frequency bands, characterized in that electric signals from an acoustic to electric transducer are separated into component signals in band pass filters of frequency band widths (curve 54', FIG. 2) substantially corresponding to the frequency resolution capability of hearing (curve 54, FIG. 2), the latter component signals then being converted into signal levels corresponding to the component signal amplitudes, and, finally, taking into account the sensation intensity per electrode and following suppression of irrelevant components, the signal levels are converted into pulse durations of current pulses which are supplied to the electrodes, wherein the band widths of the filter channels with mean frequencies above 500 Hz are somewhat greater than third band widths (curve 54'', FIG. 2), and the band widths of filter channels with mean frequencies less than 500 Hz define a band width as a function of mean frequency which is relatively independent of the mean frequency and is approximated by a constant band width of approximately 130 Hz to 150 Hz.

21. A method according to claim 20, wherein the component signals from the band pass filters are supplied to half-wave rectifiers and charging capacitors to produce said signal levels, and the signal levels are supplied, via an analog-to-digital converter (39) and a multiplexer (35), to a process control computer (41), and periodically the signal levels are erased at the capacitors, so that, in uniform time intervals ($T_a$), the maximum values of the component signals from the band pass filters are formed as said signal levels.

22. A method according to claim 21, wherein the uniform time interval ($T_a$) for charging of the capacitors is greater than the maximally occurring fundamental frequency period and hence is greater than or equal to ten milliseconds.

23. Apparatus for carrying out the method according to claim 20, with a microphone (20) producing the electric signals, an amplifier (21) connected with the microphone and having a frequency dependent response for achieving a compensation of the level drop toward high frequencies in the case of speech spectra, a dynamic limiter (22) connected with said amplifier (21), an arrangement (23) of band pass filters (24 through 26) coupled with the limiter (22), an arrangement (28) of peak voltage formation elements (29 to 31) connected with the outputs of the band pass filters (24 through 26), and a cancel switch (33 to 34) coupled with each respective peak value formation element for erasing the associated signal level after each of a succession of sampling intervals, and a multiplexer (35) having inputs connected with the respective peak voltage formation elements (29 to 31) and having a multiplexer output for supplying respective signal levels during the successive sampling intervals, a computer (41) connected with the multiplexer output, and a current source arrangement (47) for supplying electrodes (74 through 77) with stimulation signals connected with said computer (41).

* * * * *